United States Patent [19]

Stephan

[11] Patent Number: 4,732,752

[45] Date of Patent: Mar. 22, 1988

[54] POLYVALENT EQUINE IMMUNE SERUM COMPOSITION AND METHOD FOR TREATING RHEUMATOID ARTHRITIS

[75] Inventor: Peter M. Stephan, London, England

[73] Assignee: Peter Stephan Center, Ltd., Miami, Fla.

[21] Appl. No.: 922,386

[22] Filed: Oct. 23, 1986

[51] Int. Cl.$^4$ ............................................. A61K 39/395
[52] U.S. Cl. ...................................... 424/85; 530/387; 424/88
[58] Field of Search .................... 424/85, 88; 530/387

[56] References Cited

U.S. PATENT DOCUMENTS

| | | | |
|---|---|---|---|
| 3,664,994 | 5/1972 | Perper | 424/85 X |
| 4,160,825 | 7/1979 | Sikes | 424/85 |
| 4,619,827 | 10/1986 | Bull et al. | 424/88 X |
| 4,645,748 | 2/1987 | Hurwitz et al. | 530/380 |
| 4,689,224 | 8/1987 | Bull et al. | 424/85 X |

Primary Examiner—Howard E. Schain
Attorney, Agent, or Firm—Fleit, Jacobson, Cohn & Price

[57] ABSTRACT

A composition and method for treating rheumatoid arthritis, osteoarthritis, and related diseases which comprises administering an effective amount of an equine immune serum, in dosage form, to a patient. The equine immune serum is obtained from horses which have been immunized with a solution containing tissue from prenatal or pregnant pigs.

8 Claims, No Drawings

POLYVALENT EQUINE IMMUNE SERUM COMPOSITION AND METHOD FOR TREATING RHEUMATOID ARTHRITIS

BACKGROUND OF THE INVENTION

1. Field of the Invention

The present invention relates to a composition and method for treating rheumatoid arthritis, osteoarthritis, non-specific rheumatism and other related diseases in humans.

2. Brief Description of Prior Art

Arthritis is a term generally used to describe a condition of inflamed joints which is characterized by pain and swelling. Both osteoarthritis and rheumatoid arthritis may result in stiffness, swelling and a considerable amount of pain. Treatment generally includes rest, the application of heat, and the administration of anti-inflammatory drugs. Often, the treatment further includes the administration of disease-modifying anti-rheumatic drugs such as gold, methotrexate and penicillamine. However, since these drugs are quite toxic and often result in serious side-effects, they must be used with caution. In view of the severity of rheumatoid arthritis, osteoarthritis, and other related diseases, there is a great need for a drug which is easily tolerated and free from serious side-effects.

Thus, it is an object of the present invention to provide a novel composition for the treatment of rheumatoid arthritis, osteoarthritis, and related diseases.

It is a further object of the present invention to provide a composition which offers relief from the symptoms of rheumatoid arthritis, osteoarthritis, and related diseases without inducing serious side-effects.

A still further object of the present invention is to provide an equine immune serum which is non-toxic and significantly reduces the debilitating effects of arthritic type diseases.

An additional object of the present invention is to provide an equine immune serum containing antibodies to tissue from prenatal or pregnant pigs which is effective in treating rheumatoid arthritis and related diseases.

SUMMARY OF THE INVENTION

The present invention provides a novel composition for the treatment of rheumatoid arthritis, osteoarthritis, and related diseases which comprises a polyvalent equine immune serum, containing antibodies to tissue from prenatal or pregnant pigs in an inert pharmaceutically acceptable carrier. The present invention also includes a method of treating rheumatoid arthritis which comprises administering an effective amount of the equine immune serum to a patient.

Generally, one dose of the composition of the present invention contains from 0.15 to 1.25 mls of the polyvalent equine immune serum as the active ingredient. The composition of the present invention may be administered in suppository form or by intradermal injection. Generally, one half to one dose of the serum preparation is administered between about 2 to 10 times per week to a patient suffering from rheumatoid arthritis or a related disease. However, the equine immune serum can be administered at an amount between 0.5 to 5 doses per day.

DESCRIPTION OF THE PREFERRED EMBODIMENTS

The polyvalent equine immune serum of the present invention is prepared by injecting a horse with a suspension of the macerated organs of adult pigs or pigs which are taken from the mother pig immediately preceding or at the moment of birth. It is possible to use any and all organs and tissues of the pigs in preparing the antigens for injection into a horse. However, in a preferred embodiment, the bone marrow, bone tissue, thymus, spleen, lymphatic ganglia, parathyroid gland, connective tissue, and serous membranes of prenatal pigs are utilized. The organs and tissues are homogenized and suspended in a sterile saline solution using procedures which are known in the art. The antigen containing solution is injected into a horse at repeated intervals and the blood and serum of the horse is regularly tested for levels of antibodies. The serum containing antibodies to the tissues of the prenatal or pregnant pigs is collected from the horse when the level of serum antibodies reaches a titer of at least 100. The serum then is utilized as the polyvalent equine immune serum of the present invention.

Generally, the equine immune serum is administered in amounts from about 0.15 to about 1.25 mls per dose. Preferably, however, a typical dose contains about 0.33 mls of polyvalent equine immune serum. This typical dose contains about 60–75 mg of protein per ml.

In a preferred embodiment, the composition of the present invention is administered in suppository form. While any suitable carrier may be used in the suppositories of the present invention, a preferred carrier is propylene glycol, methyl paraben, propyl paraben, and Witepsol H15 and E75. However, the equine immune serum can also be administered by intradermal injection in any pharmaceutically acceptable carrier.

Applicants have discovered that the equine immune serum of the present invention is effective when one dosage amount of the serum preparation is administered to a patient with rheumatoid arthritis or osteoarthritis approximately five times per week. However, the serum can be administered in a dosage amount of between 0.5 to 5 doses per day.

The preferred dosage amount results in a significant improvement in the clinical parameters of pain, swelling, and walking tolerance, and provides a general increase in joint mobility in patients suffering from rheumatoid arthritis. Further, these patients do not suffer any of the side-effects of the steroidal or non-steroidal, anti-inflammatory, or disease-modifying drugs presently known.

To facilitate understanding the advantages and properties of the present invention, the following example is provided to specifically illustrate the use of the equine immune serum of the present invention.

EXAMPLE

To prepare the equine immune serum of the present invention, ten prenatal pigs were removed from a mother pig at the moment of birth. The bone marrow, bone tissue, thymus, spleen, lymphatic ganglia, parathyroid gland, connective tissue, and serous membranes were removed from each prenatal pig, homogenized, and suspended in a sterile 15% saline solution to form the antigen-containing solution for use in generating the equine immune serum. The antigen-containing solution was injected into a horse at regular intervals of approximately once a week. The antibody levels in the horse serum were checked regularly, and when the antibody levels in the serum reached a titer of at least 100, the equine immune serum was suitable for use in the present composition for treating rheumatoid arthritis.

The equine immune serum, as the active ingredient, was prepared for administration to humans by combining the serum with inactive pharmaceutically acceptable ingredients in a suppository form. A single dosage suppository of the composition of the present invention contained the following ingredients, in the indicated quantities:

| Active Ingredients | Equine immune serum (specific to bone marrow, bone tissue, thymus, spleen, lymphatic ganglia, parathyroid gland, connective tissue, serous membranes) | 0.33 ml (60 mg protein/ml) |
|---|---|---|
| Inactive Ingredients | Propylene glycol | 103.80 mg |
| | Methyl paraben | 1.10 mg |
| | Propyl paraben | 2.20 mg |
| | Witepsol H15 | 744.60 mg |
| | Witepsol E75 | 510.00 mg |

Between Jan. 6 and Aug. 26, 1986, 40 patients with proven sero-positive rheumatoid arthritis, all with active disease, were entered into a study of the efficacy of the polyvalent equine immune serum of the present invention. The study was a double-blind, placebo-controlled study. Patients with sero-positive rheumatoid arthritis represent, as a group, the most severe and crippling form of any arthritis. During the study, corticosteroids and chemotherapy were not permitted as a form of treatment. However, since the group as a whole represents very ill patients, non-steroidal anti-inflammatory drugs were permitted and sometimes prescribed for an individual patient.

Each patient who received the immune serum of the present invention was administered a suppository containing 0.33 mls of active ingredient as described above at intervals of five suppositories a week. At the end of the first 12 weeks, 50% of the placebo-controlled group improved while receiving only non-steroidal anti-inflammatory drugs. On the other hand, 90% of the patients who received the immune serum of the present invention were clinically improved at the end of the first 12 weeks. Further, some patients responded well to the equine immune serum when they previously had received little relief with disease-modifying anti-rheumatic drugs such as gold, methotrexate, and penicillamine.

Significantly, the immune serum given in suppository form is very well tolerated and free of untoward clinical side-effects. In addition, no abnormalities were encountered in any of the laboratory results. These observations are in sharp contrast to the near 100% side-effects and laboratory abnormalities encountered in all of the non-steroidal, anti-inflammatory drugs and to even a greater degree in the disease-modifying anti-rheumatic drugs.

As will be readily understood by those of ordinary skill in the art, minor modifications may be made in the invention described above without in any way departing from the spirit and scope of the invention. Accordingly, it is understood that the invention will not be limited to the exact details disclosed herein above, but will be defined in accordance with the appended claims.

What is claimed is:

1. A therapeutic composition in dosage form comprising a pharmaceutically acceptable carrier and a polyvalent equine immune serum which contains antibodies to pig bone marrow, bone tissue, thymus, spleen, lymphatic ganglia, parathyroid gland, connective tissue, and serous membranes.

2. A composition according to claim 1 wherein said pharmaceutically acceptable carrier is in the form of a suppository.

3. A composition according to claim 1 wherein said pharmaceutically acceptable carrier is in a form suitable for injection.

4. A composition according to claim 1 wherein said equine immune serum is present in an amount of between about 0.15 and 1.25 mls per dose.

5. A method of treating rheumatoid arthritis, osteoarthritis, and other related diseases which comprises administering to a patient having rheumatoid arthritis, osteoarthritis or a related disease, an effective amount of a composition having as the essential active ingredient a polyvalent equine immune serum containing antibodies to pig bone marrow, bone tissue, thymus, spleen, lymphatic ganglia, parathyroid gland, connective tissue, and serous membranes.

6. A method according to claim 5 wherein said composition is administered in suppository form.

7. A method according to claim 5 wherein said composition is administered by injection.

8. A method according to claim 5 wherein said effective amount is 0.15 to 1.25 mls per dose.

* * * * *